(12) United States Patent
Choi et al.

(10) Patent No.: US 11,786,151 B2
(45) Date of Patent: Oct. 17, 2023

(54) APPARATUS AND METHOD FOR OBTAINING TARGET SIGNAL SPECTRUM

(71) Applicant: SAMSUNG ELECTRONICS CO., LTD., Suwon-si (KR)

(72) Inventors: Ka Ram Choi, Hwaseong-si (KR); So Young Lee, Daejeon (KR); Jun Ho Lee, Incheon (KR); Sang Kyu Kim, Yongin-si (KR); Hyeong Seok Jang, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 398 days.

(21) Appl. No.: 17/119,634

(22) Filed: Dec. 11, 2020

(65) Prior Publication Data

US 2022/0054050 A1 Feb. 24, 2022

(30) Foreign Application Priority Data

Aug. 24, 2020 (KR) .................. 10-2020-0106001

(51) Int. Cl.
*A61B 5/1455* (2006.01)
*A61B 5/145* (2006.01)
(Continued)

(52) U.S. Cl.
CPC ........ *A61B 5/1455* (2013.01); *A61B 5/14532* (2013.01); *A61B 5/14546* (2013.01);
(Continued)

(58) Field of Classification Search
CPC .............. A61B 5/1455; A61B 5/14532; A61B 5/14546; A61B 5/4866; A61B 5/7203;
(Continued)

(56) References Cited

U.S. PATENT DOCUMENTS 7,460,895 B2 12/2008 Arnold et al.
7,734,321 B2 6/2010 White
(Continued)

FOREIGN PATENT DOCUMENTS

JP 5964773 B2 8/2016
JP 2018-21833 A 2/2018
(Continued)

OTHER PUBLICATIONS

Chamathca P.S. Kuda-Malwathumullage et al., "Temperature correction strategy for improving concentration predictions with near-infrared spectra of aqueous-based samples", Analytica Chimica Acta 1095, Sep. 14, 2019, pp. 20-29 (10 pages total).
(Continued)

*Primary Examiner* — David J. McCrosky
*Assistant Examiner* — Clarissa Cuevas
(74) *Attorney, Agent, or Firm* — Sughrue Mion, PLLC

(57) ABSTRACT

An apparatus for obtaining a target signal spectrum includes: a spectrum measurer configured to measure a plurality of spectra from an object; and a processor configured to obtain a difference spectrum matrix by subtracting a reference spectrum from each of the plurality of spectra, and to obtain a spectrum of a target signal based on the obtained difference spectrum matrix.

17 Claims, 14 Drawing Sheets

(51) Int. Cl.
  *A61B 5/00* (2006.01)
  *G16H 40/60* (2018.01)
(52) U.S. Cl.
  CPC .......... *A61B 5/4866* (2013.01); *A61B 5/7203* (2013.01); *A61B 5/7257* (2013.01); *G16H 40/60* (2018.01); *A61B 2560/0431* (2013.01); *A61B 2562/0233* (2013.01)
(58) Field of Classification Search
  CPC .......... A61B 5/7257; A61B 2562/0233; G16H 40/60
  See application file for complete search history.

(56) References Cited

U.S. PATENT DOCUMENTS

| | | | |
|---|---|---|---|
| 7,873,397 B2 | 1/2011 | Higgins et al. | |
| 10,206,577 B2 | 2/2019 | Jang et al. | |
| 10,506,989 B2 | 12/2019 | Maruo | |
| 10,753,797 B2 | 8/2020 | Kim et al. | |
| 2005/0203358 A1 | 9/2005 | Monfre et al. | |
| 2007/0084990 A1 | 4/2007 | Coates | |
| 2010/0160750 A1 | 6/2010 | White et al. | |
| 2010/0165338 A1* | 7/2010 | Claps | G01J 3/0256 356/317 |
| 2010/0249546 A1 | 9/2010 | White | |
| 2012/0166092 A1* | 6/2012 | Maruo | A61B 5/1455 702/19 |
| 2016/0103063 A1 | 4/2016 | Kurasawa et al. | |
| 2017/0027526 A1* | 2/2017 | Maruo | A61B 5/1455 |
| 2017/0319066 A1 | 11/2017 | Ver Steeg et al. | |
| 2018/0146899 A1 | 5/2018 | Lee et al. | |
| 2018/0188117 A1 | 7/2018 | Matousek et al. | |
| 2018/0232581 A1 | 8/2018 | Reinpoldt et al. | |
| 2019/0117136 A1 | 4/2019 | Lee et al. | |
| 2019/0154656 A1 | 5/2019 | Bae et al. | |
| 2019/0159680 A1 | 5/2019 | Tanaka et al. | |
| 2019/0313914 A1 | 10/2019 | Kirenko et al. | |
| 2020/0025612 A1* | 1/2020 | Kim | G01J 3/2823 |
| 2020/0037884 A1 | 2/2020 | Ishida et al. | |
| 2020/0107759 A1 | 4/2020 | Lee | |
| 2020/0121244 A1 | 4/2020 | Lee et al. | |

FOREIGN PATENT DOCUMENTS

| | | |
|---|---|---|
| JP | 2019-531825 A | 11/2019 |
| KR | 10-2010-0054131 A | 5/2010 |
| KR | 10-2019-0057743 A | 5/2019 |
| KR | 10-2020-0009869 A | 1/2020 |

OTHER PUBLICATIONS

Peter Snoer Jensen et al., "Influence of Temperature on Water and Aqueous Gluclose Absorption Spectra in the Near-and Mid-Infrared Regions at Physiologically Relevant Temperatures", Applied Spectroscopy, Aug. 24, 2002, vol. 57, No. 1, pp. 28-36 (9 pages total).
Communication dated Jan. 24, 2022 by the European Patent Office in European Patent Application No. 21190304.2.
Gunga et al., "A non-invasive device to continuously determine heat strain in humans," ELSEVIER, Journal of Thermal Biology, vol. 33, pp. 297-307, 2008, 12 pages.

* cited by examiner

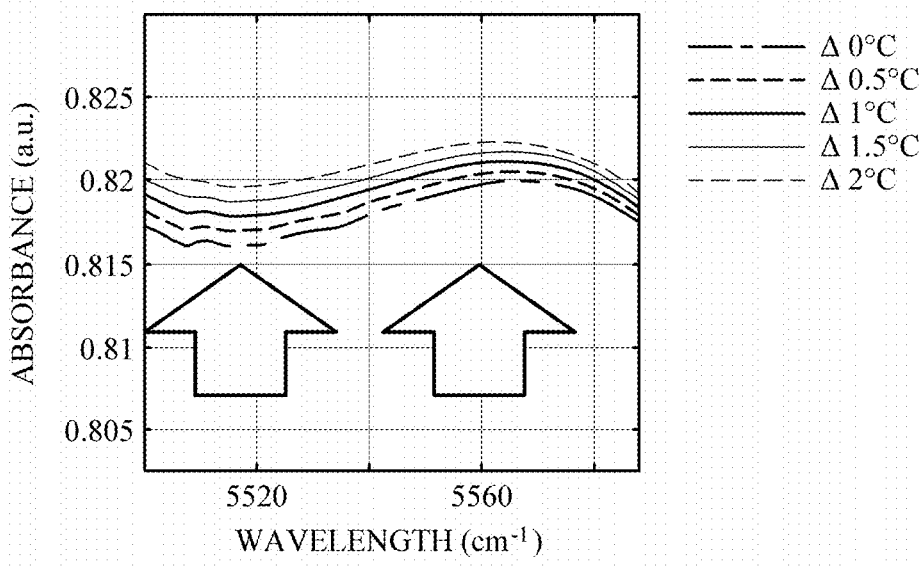

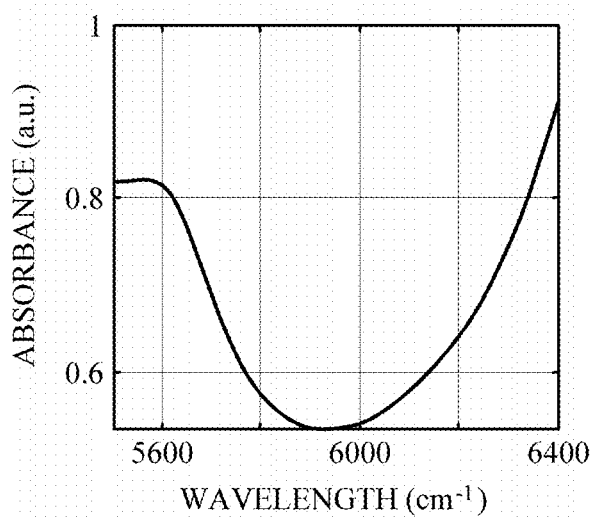

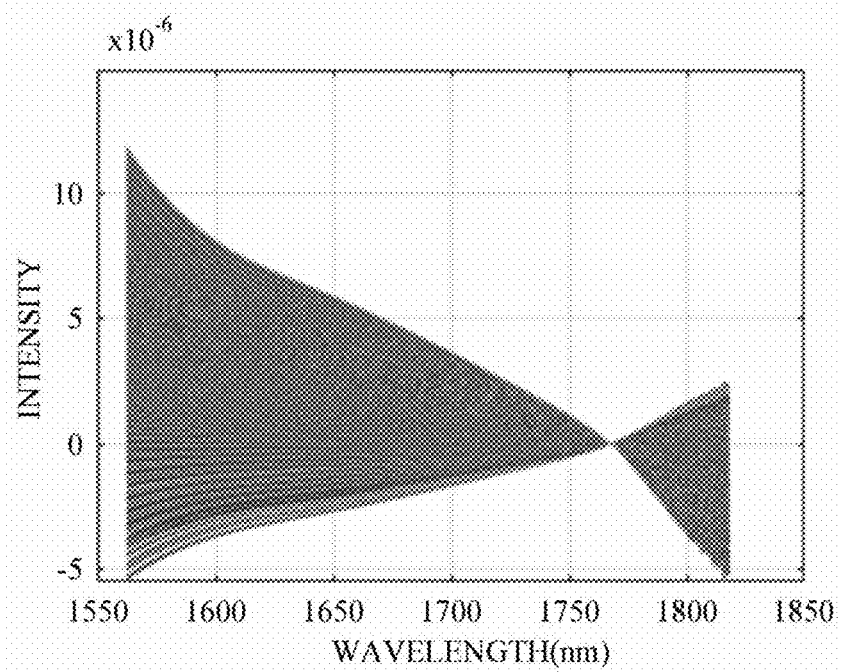

APPARATUS AND METHOD FOR OBTAINING TARGET SIGNAL SPECTRUM

CROSS-REFERENCE TO RELATED APPLICATION(S)

This application claims priority from Korean Patent Application No. 10-2020-0106001, filed on Aug. 24, 2020, in the Korean Intellectual Property Office, the entire disclosure of which is herein incorporated by reference for all purposes.

BACKGROUND

1. Field

Example embodiments of the disclosure relate to obtaining a target signal spectrum for non-invasively estimating a target signal.

2. Description of the Related Art

Diabetes is a chronic disease that can cause various complications and is hardly curable. Therefore, patients with diabetes are advised to check their blood glucose regularly to prevent complications. In particular, when insulin is administered to control blood glucose, the blood glucose levels have to be closely monitored to avoid hypoglycemia and control insulin dosage. An invasive method of finger pricking is generally used to measure blood glucose levels. However, while the invasive method may provide high reliability in measurement, it may cause pain and inconvenience as well as an increased risk of disease infections due to the use of injection. Recently, research has been conducted on methods of non-invasively estimating bio-information, such as blood glucose, by spectrum analysis using a spectrometer without blood sampling.

SUMMARY

In accordance with an aspect of an example embodiment, there is provided an apparatus for obtaining a target signal spectrum, the apparatus including: a spectrum measurer configured to measure a plurality of spectra from an object; and a processor configured to obtain a difference spectrum matrix by subtracting a reference spectrum from each of the plurality of spectra, and to obtain a spectrum of a target signal based on the obtained difference spectrum matrix.

The spectrum measurer may include: a light source configured to emit light onto the object; and a detector configured to detect light scattered or reflected from the object.

The spectrum measurer may measure the plurality of spectra continuously at predetermined time intervals in an in-vivo environment or an in-vitro environment where the target signal changes.

The reference spectrum may include, among the plurality of spectra, at least one of a spectrum measured at a predetermined time, an average spectrum of the plurality of spectra, a spectrum measured in a fasting state when the plurality of spectra are measured in the in-vivo environment, or a spectrum measured in an aqueous solution when the plurality of spectra are measured in the in-vitro environment.

The processor may remove noise from the measured plurality of spectra based on one or more of second-order differentiation, filtering, asymmetric least square (ALS), detrend, multiplicative scatter correction (MSC), extended multiplicative scatter correction (EMSC), standard normal variate (SNV), mean centering (MC), fourier transform (FT), orthogonal signal correction (OSC), and Savitzky-Golay smoothing (SG).

The processor may obtain a symmetric matrix by calculating an inner product between the difference spectrum matrix and a transposed matrix of the difference spectrum matrix, and may obtain the spectrum of the target signal by using the obtained symmetric matrix.

The processor may select one row or one column from the obtained symmetric matrix, and may obtain the spectrum of the target signal based on the selected one row or one column.

The processor may select the one row or the one column from the obtained symmetric matrix based on a degree of change in the target signal.

The processor may select a row or a column of a wavelength, at which a degree of change in the target signal is greatest, or a row or a column of a wavelength, at which a degree of absorption of the target signal is highest, from the obtained symmetric matrix.

The processor may calculate an inner product between a shift vector of a predetermined wavelength and shift vectors of other wavelengths in the difference spectrum matrix, and may obtain the spectrum of the target signal based on the calculated inner product.

The processor may scale an amplitude of the obtained spectrum of the target signal to correspond to an amplitude of a reference target signal spectrum.

The target signal may include one or more of an antioxidant-related substance, blood glucose, triglyceride, cholesterol, calories, protein, carotenoid, lactate, and uric acid.

In accordance with an aspect of an example embodiment, there is provided a method of obtaining a target signal spectrum, the method including: measuring a plurality of spectra; obtaining a difference spectrum matrix by subtracting a reference spectrum from each of the plurality of spectra; and obtaining a spectrum of a target signal based on the obtained difference spectrum matrix.

The reference spectrum may include, among the plurality of spectra, at least one of a spectrum measured at a predetermined time, an average spectrum of the plurality of spectra, a spectrum measured in a fasting state when the plurality of spectra are measured in the in-vivo environment, or a spectrum measured in an aqueous solution when the plurality of spectra are measured in the in-vitro environment.

In addition, the method of obtaining a target signal spectrum may further include removing noise from the measured plurality of spectra based on one or more of second-order differentiation, filtering, asymmetric least square (ALS), detrend, multiplicative scatter correction (MSC), extended multiplicative scatter correction (EMSC), standard normal variate (SNV), mean centering (MC), fourier transform (FT), orthogonal signal correction (OSC), and Savitzky-Golay smoothing (SG).

The obtaining of the spectrum of the target signal may include: obtaining a symmetric matrix by calculating an inner product between the difference spectrum matrix and a transposed matrix of the difference spectrum matrix; and obtaining the spectrum of the target signal by using the symmetric matrix.

The obtaining of the spectrum of the target signal by using the symmetric matrix may include: selecting one row or one column from the obtained symmetric matrix; and obtaining the spectrum of the target signal based on the selected one row or one column.

The obtaining of the spectrum of the target signal by using the symmetric matrix may include selecting the one row or the one column from the obtained symmetric matrix based on a degree of change in the target signal.

The obtaining of the spectrum of the target signal may include: calculating an inner product between a shift vector of a predetermined wavelength and shift vectors of other wavelengths in the difference spectrum matrix; and obtaining the spectrum of the target signal based on the calculated inner product.

The obtaining of the spectrum of the target signal may include scaling an amplitude of the obtained spectrum of the target signal to correspond to an amplitude of a reference target signal spectrum.

BRIEF DESCRIPTION OF THE DRAWINGS

The above and other aspects, features, and advantages of certain example embodiments of the disclosure will be more apparent from the following description taken in conjunction with the accompanying drawings, in which:

FIGS. 2A to 2C are diagrams explaining a correlation between a target signal and wavelengths;

FIGS. 3A to 3D are diagrams illustrating an example of obtaining a target signal spectrum;

DETAILED DESCRIPTION

Figure 1:
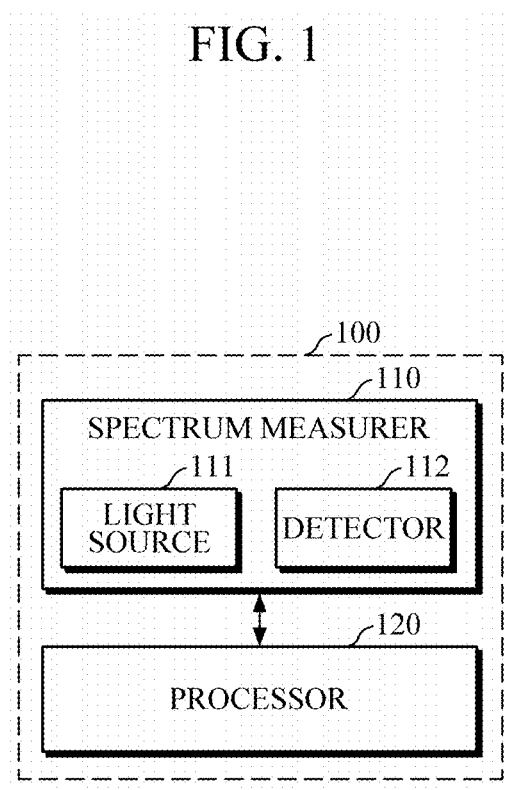
FIG. 1 is a block diagram illustrating an apparatus for obtaining a target signal spectrum according to an example embodiment.

Details of example embodiments are included in the following detailed description and drawings. Advantages and features of the disclosure, and a method of achieving the same will be more clearly understood from the following embodiments described in detail with reference to the accompanying drawings. Throughout the drawings and the detailed description, unless otherwise described, the same drawing reference numerals will be understood to refer to the same elements, features, and structures. The relative size and depiction of these elements may be exaggerated for clarity, illustration, and convenience.

It will be understood that, although the terms first, second, etc. may be used herein to describe various elements, these elements should not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as 'unit' or 'module', etc., should be understood as a unit that performs at least one function or operation and that may be embodied as hardware, software, or a combination thereof.

FIG. 1 is a block diagram illustrating an apparatus for obtaining a target signal spectrum according to an example embodiment.

Referring to FIG. 1, the apparatus 100 for obtaining a target signal spectrum includes a spectrum measurer 110 and a processor 120.

The spectrum measurer 110 may measure a spectrum from an object in an in-vivo environment or in an in-vitro environment. In the case where a target signal spectrum is obtained in an in-vivo environment, the object may be skin of the human body; and in the case where a target signal spectrum is obtained in an in-vitro environment, the object may be an aqueous solution containing a target signal or a composite material containing component signals other than the target signal.

The spectrum measurer 110 may include, for example, a spectrometer for measuring a spectrum over a wide wavelength range. The spectrometer may use various spectroscopic techniques, such as Infrared spectroscopy using near-infrared light or mid-infrared light, Raman spectroscopy, and the like. In another example, the spectrum measurer 110 may include an optical sensor for measuring a spectrum over a narrow wavelength range.

The spectrometer or the optical sensor may include one or more light sources for emitting light onto the object, and one or more detectors for detecting light scattered or reflected from the object. The light source may include a light emitting diode (LED), a laser diode (LD), a phosphor, and the like. The detector may include a photo diode, a photo transistor (PTr), an image sensor (e.g., CMOS image sensor), and the like, but is not limited thereto.

The spectrum measurer 110 may measure a plurality of spectra from the object. For example, the spectrum measurer 110 may measure a spectrum of a target signal continuously at predetermined time intervals in an environment where the target signal changes. The target signal may include anti-oxidant-related substances, blood glucose, triglyceride, cholesterol, calories, protein, carotenoid, lactate, uric acid, and the like. However, the target signal is not limited thereto and may be a noise signal such as temperature, humidity, and the like.

For example, a spectrum of a blood glucose signal may be measured in the in-vivo environment by increasing or decreasing an amount of sugar intake at predetermined time intervals. The plurality of spectra, measured by the spectrum measurer 110, may include spectra of various body substances and/or noise components (e.g., temperature, humidity, etc.), and the like, in addition to the spectrum of the blood glucose signal. In an example, a spectrum of a temperature signal may be measured in the in-vivo environment by increasing or decreasing the temperature at predetermined time intervals.

In another example, a spectrum of a blood glucose signal may be measured in the in-vitro environment by, for example, increasing blood glucose levels at predetermined time intervals in an aqueous solution or in a composite material solution containing blood glucose and other substances. Further, a spectrum of a temperature signal may be measured in the in-vitro environment by increasing or decreasing the temperature of an aqueous solution containing blood glucose or a composite material solution containing blood glucose at predetermined time intervals.

The processor 120 may obtain a target signal spectrum by considering a correlation between a target signal and wavelengths based on the plurality of spectra measured by the spectrum measurer 110.

Figure 2A:
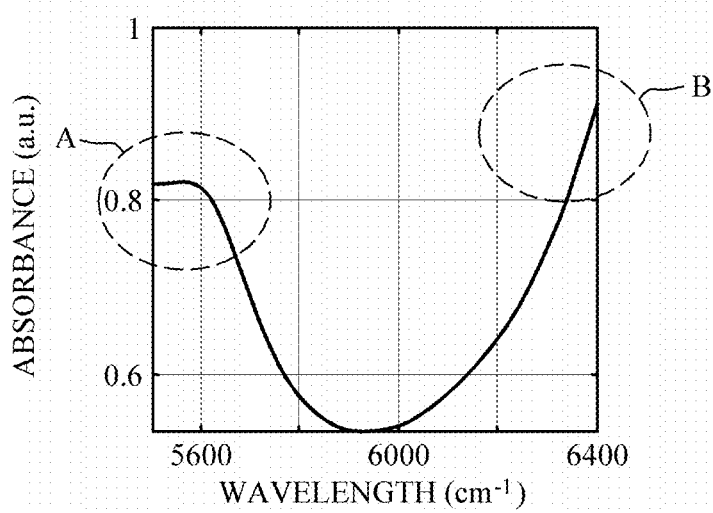
Figure 2C:
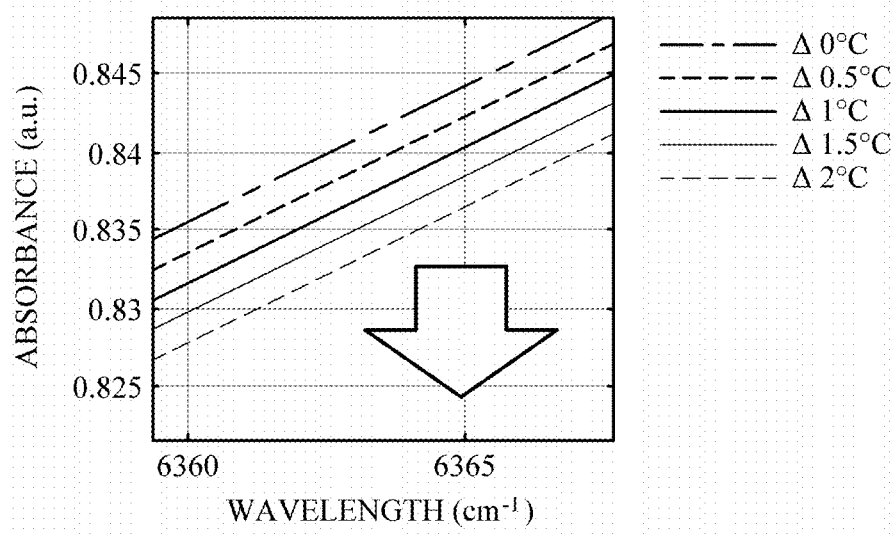

FIGS. 2A to 2C are diagrams explaining a correlation between a target signal and wavelengths. FIG. 2A illustrates spectra obtained by changing temperature of an aqueous solution. FIG. 2B is an enlarged view of the spectra in a wavelength range A around 5600 cm$^{-1}$ of FIG. 2A. FIG. 2C is an enlarged view of the spectra in a wavelength range B around 6400 cm$^{-1}$ of FIG. 2A.

Referring to FIG. 2B, it can be seen that as temperature gradually increases in a relatively low wavelength range A, absorbance also increases. Referring to FIG. 2C, it can be seen that as temperature gradually increases in a relatively high wavelength range B, absorbance decreases. That is, with respect to the spectrum at the wavelength of 5520 cm$^{-1}$ and the spectrum at the wavelength of 5560 cm$^{-1}$, spectral absorbance values, which are changed with the increase in temperature, are positive such that spectral covariance values at the two wavelengths 5520 cm$^{-1}$ and 5560 cm$^{-1}$ are positive, thereby indicating a positive correlation. By contrast, with respect to the spectrum at the wavelength of 5520 cm$^{-1}$, spectral absorbance values, which are changed with the increase in temperature, are positive, and with respect to the spectrum at the wavelength of 6360 cm$^{-1}$, spectral absorbance values, which are changed with the increase in temperature, are negative such that spectral covariance values at the two wavelengths 5520 cm$^{-1}$ and 6360 cm$^{-1}$ are negative, thereby indicating a negative correlation.

In an embodiment, the target signal spectrum changes differently for each wavelength, such that the target signal spectrum may be obtained by considering a correlation between a target signal and each wavelength.

Figure 3B:
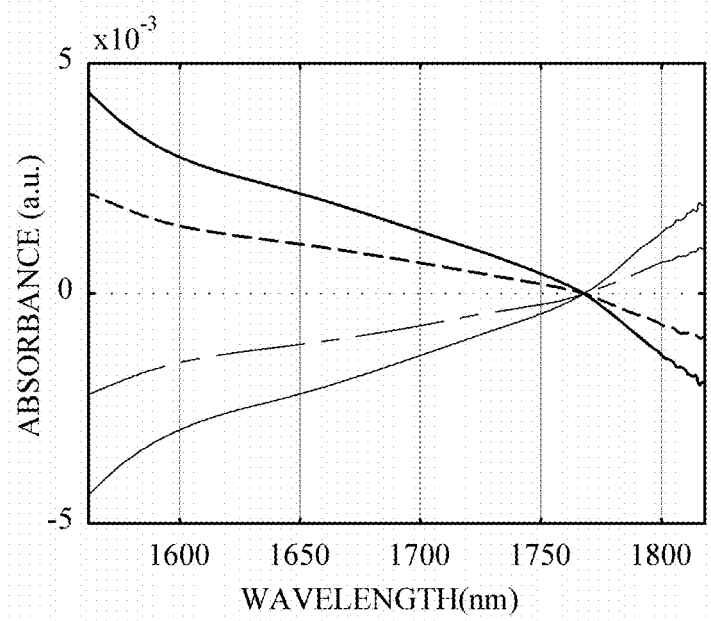

FIGS. 3A to 3D are diagrams illustrating an example of obtaining a target signal spectrum. FIGS. 4A and 4B are diagrams explaining an example of obtaining a target signal spectrum in an in-vivo environment and an in-vitro environment.

FIG. 3A illustrates a plurality of spectra obtained by the spectrum measurer 110 in an environment where the target signal changes. The spectrum measurer 110 may measure the spectra at a calibration time by gradually changing the target signal at predetermined time intervals in the in-vivo or in-vitro environment as described above. The following Equation 1 is an example of a spectrum matrix.

$$X = \begin{bmatrix} x_{11} & \cdots & x_{1m} \\ \vdots & \ddots & \vdots \\ x_{n1} & \cdots & x_{nm} \end{bmatrix}$$ [Equation 1]

Here, X denotes an m number of spectra, expressed in an n×m matrix, and obtained by changing the target signal an m number of times with respect to an n number of wavelengths.

Upon measuring the plurality of spectra, the processor 120 may remove noise from the measured spectra. For example, the processor 120 may remove noise based on first-order differentiation, second-order differentiation, filtering, asymmetric least square (ALS), detrend, multiplicative scatter correction (MSC), extended multiplicative scatter correction (EMSC), standard normal variate (SNV), mean centering (MC), fourier transform (FT), orthogonal signal correction (OSC), Savitzky-Golay smoothing (SG), and the like. Further, as illustrated in FIG. 3B, the processor 120 may obtain a difference spectrum matrix by subtracting a reference spectrum from each of the measured spectra. The following Equation 2 represents a difference spectrum matrix obtained by subtracting the reference spectrum from each of the measured spectra.

$$D = X - X_{ref}$$ [Equation 2]

Herein, D denotes the difference spectrum matrix, and $X_{ref}$ denotes an n×1 matrix of the reference spectrum. For example, the reference spectrum may be pre-obtained. For example, when measured in the in-vivo environment, the reference spectrum may be a spectrum measured when a user is in a fasting state. Alternatively, when measured in the in-vitro environment, the reference spectrum may be a spectrum measured in an aqueous solution. In another example, the reference spectrum may be obtained based on the plurality of spectra measured by the spectrum measurer 110. For example, among the plurality of spectra, the reference spectrum may be, for example, a first spectrum, an intermediate spectrum, or a last spectrum. Alternatively, the reference spectrum may be an average of all the measured spectra, or an average of spectra in a specific interval. However, the reference spectrum is not limited thereto.

Upon obtaining the difference spectrum matrix, the processor 120 may generate a symmetric matrix by calculating an inner product between the difference spectrum matrix and a transposed matrix of the difference spectrum matrix, as represented by the following Equation 3. FIG. 3C illustrates the spectra generated according to the symmetric matrix.

$$M = D \cdot D^T$$ [Equation 3]

Herein, M denotes the symmetric matrix, and D denotes the difference spectrum matrix; $D^T$ denotes the transposed matrix of the difference spectrum matrix. The symmetric matrix may be an n×n matrix, with n being the number of wavelengths. The processor 120 may normalize the obtained symmetric matrix based on m number of spectra.

Figure 3D:
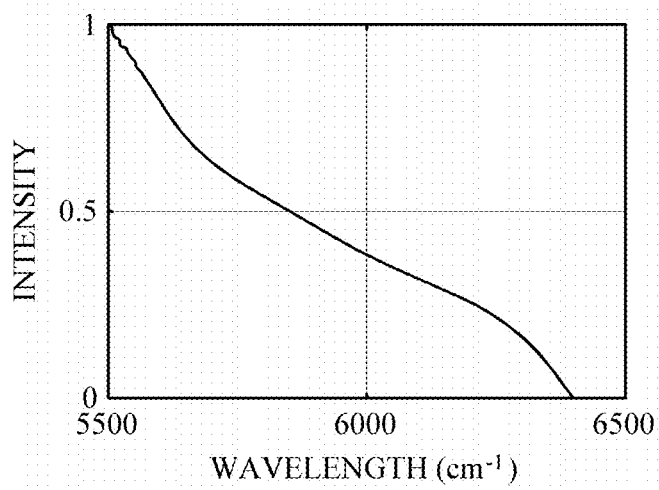
Figure 4A:
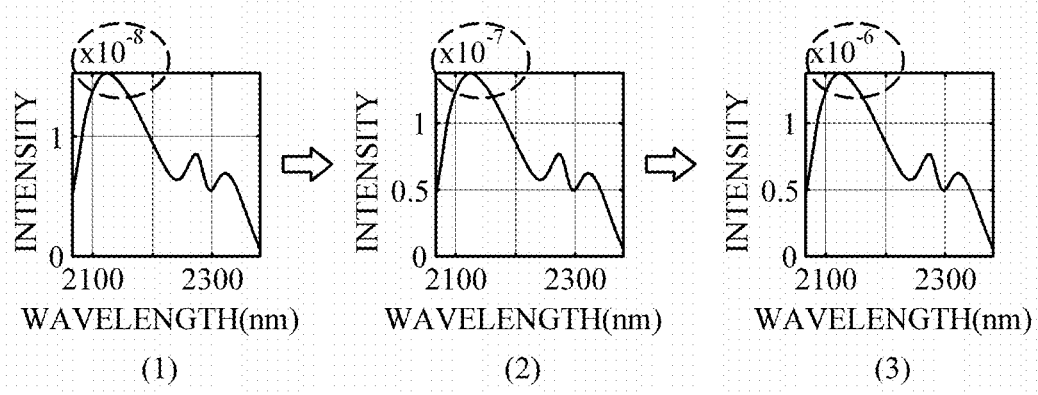
FIGS. 4A and 4B are diagrams explaining an example of obtaining a target signal spectrum from a composite material and an aqueous solution.
Figure 4B:
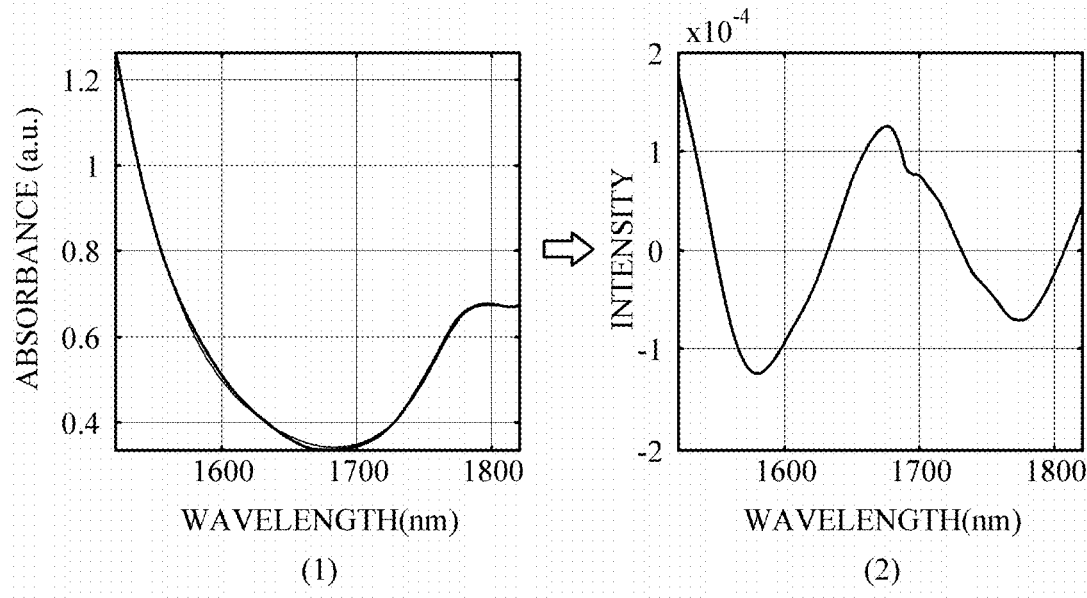

Then, the processor 120 may select any one row or column from the generated symmetric matrix as represented by the following Equation 4, and may obtain the target signal spectrum based on the selected row or column, as illustrated in FIG. 3D.

$$S_t = M(k)$$ [Equation 4]

Herein, $S_t$ denotes the target signal spectrum (or a spectrum of the target signal); k denotes a specific wavelength, i.e., a specific row or column of the symmetric matrix; and M(k) denotes a spectrum at the specific wavelength k of the symmetric matrix M. In this case, k may be a row or a column of a wavelength, at which a change in the target signal is greatest, in the symmetric matrix.

Further, upon obtaining the difference spectrum as described above, the processor 120 may obtain a target signal spectrum by calculating an inner product between a shift vector of the reference wavelength and shift vectors of all the wavelengths. The reference wavelength may be a wavelength at which a change in the difference spectrum is greatest, or a wavelength at which a degree of absorption of the target signal is highest. For example, the processor 120 may obtain a target signal spectrum by calculating an inner product of shift vectors of all the wavelengths based on the shift vector corresponding to about 1580 nm, at which a change in the difference spectrum is greatest as illustrated in FIG. 3B.

Further, the shape of a target signal spectrum may vary depending on the structure of the spectrum measurer 110 and the like, such that upon obtaining the target signal spectrum as described above, the processor 120 may scale an amplitude of the target signal spectrum based on an amplitude of a reference target signal spectrum stored in a reference database, for example, to correspond to the amplitude of the reference target signal spectrum. In this case, the scaled target signal spectrum may be used as a unit spectrum for estimating the concentration of a target material.

FIG. 4A illustrates an example of a glucose signal spectrum obtained from a composite material. That is, the glucose signal spectrum is obtained from a composite material solution of lactate and glucose by gradually increasing the glucose level to (1) 5 mM, (2) 7 mM, and (3) 13 mM while maintaining the lactate level at 1 mM. It can be seen from FIG. 4A that a peak of the glucose signal spectrum changes as the glucose level increases. FIG. 4B illustrates an example of (1) a spectrum measured in an aqueous solution containing glucose, and (2) a glucose signal spectrum from which noise is removed.

Figure 5:
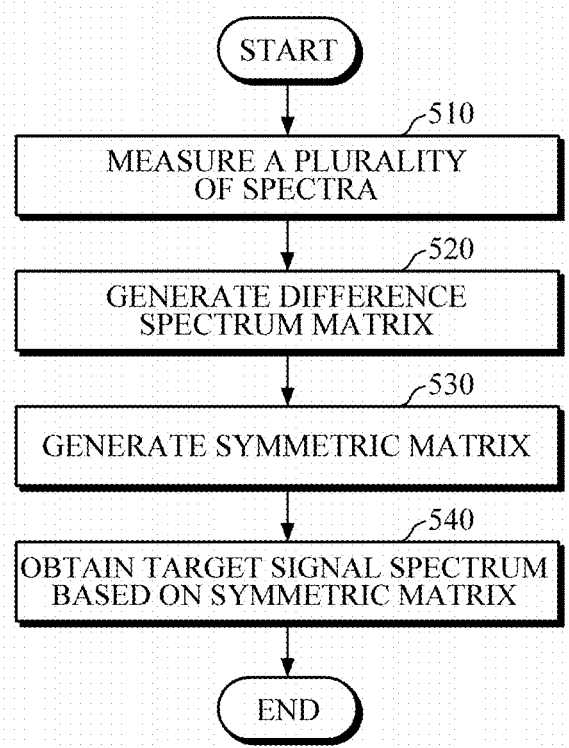
FIG. 5 is a flowchart illustrating a method of obtaining a target signal spectrum according to an example embodiment.

FIG. 5 is a flowchart illustrating a method of obtaining a target signal spectrum according to an example embodiment.

The method of FIG. 5 is an example of a method of obtaining a target signal spectrum which is performed by the apparatus 100 for obtaining a target signal spectrum according to the embodiment of FIG. 1.

The apparatus 100 for obtaining a target signal spectrum may measure a plurality of spectra from an object in 510. The target signal may be a substance to be estimated, such as blood glucose, or may be noise, such as temperature and the like, which is to be considered in estimating blood glucose and the like. The object may be skin of the human body, an aqueous solution containing the target signal, or a composite material containing the target signal and other component signals. That is, the apparatus 100 for obtaining a target signal spectrum may measure the plurality of spectra by changing the target signal to be obtained, e.g., glucose or temperature, in the in-vivo or in-vitro environment.

Then, the apparatus 100 for obtaining a target signal spectrum may obtain a difference spectrum matrix by subtracting a reference spectrum from each of the measured spectra in 520. The reference spectrum may be a spectrum measured while a user is in a fasting state, a spectrum measured in an aqueous solution, any one of the plurality of spectra measured in 510, e.g., a spectrum measured at a specific time, an average of all the measured spectra, or an average of spectra in a specific interval, and the like.

Subsequently, the apparatus 100 for obtaining a target signal spectrum may generate a symmetric matrix by multiplying a difference spectrum matrix by a transposed matrix of the difference spectrum matrix in 530. The symmetric matrix may be an n×n matrix, in which n is the number of wavelengths.

Next, the apparatus 100 for obtaining a target signal spectrum may obtain a target signal spectrum by using the symmetric matrix in 540. For example, the apparatus 100 for obtaining a target signal spectrum may select any one row or column from the symmetric matrix, and may obtain the target signal spectrum based on the selected row or column. In this case, the apparatus 100 for obtaining a target signal spectrum may select, for example, a row or a column of a wavelength at which a change in the target signal is greatest, in the symmetric matrix. Alternatively, the apparatus 100 for obtaining a target signal spectrum may select a row or a column of a preset wavelength, for example, a wavelength at which a degree of absorption of the target signal is highest.

Further, upon obtaining a spectrum of any one row or column as the target signal spectrum, the apparatus 100 for obtaining a target signal spectrum may scale an amplitude of the obtained target signal spectrum to correspond to an amplitude of a pre-defined reference target spectrum. In this case, the target signal spectrum may be used as a unit spectrum for estimating the concentration of a target material.

Figure 6:
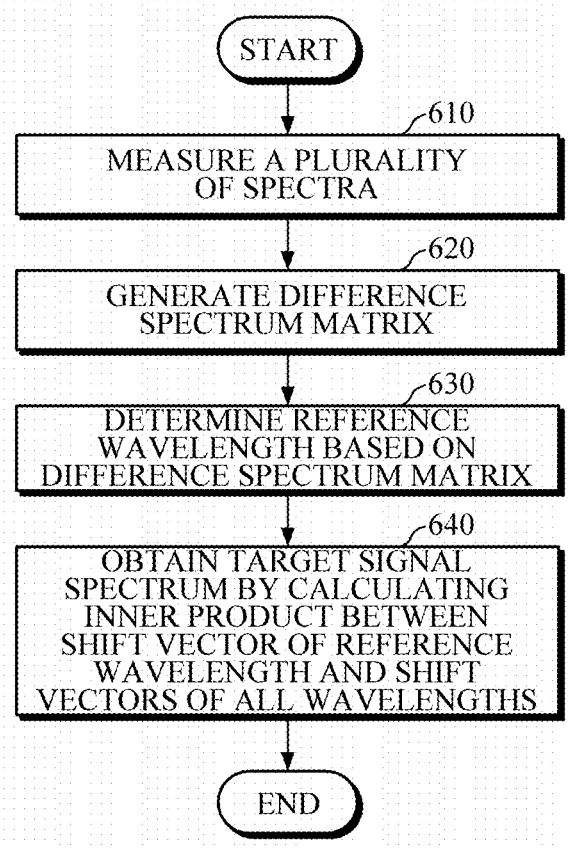
FIG. 6 is a flowchart illustrating a method of obtaining a target signal spectrum according to another example embodiment.

FIG. 6 is a flowchart illustrating a method of obtaining a target signal spectrum according to another example embodiment. The method of FIG. 6 is another example of a method of obtaining a target signal spectrum which is performed by the apparatus 100 for obtaining a target signal spectrum of FIG. 1.

The apparatus 100 for obtaining a target signal spectrum may measure a plurality of spectra from an object in 610. As described above, the apparatus 100 for obtaining a target signal spectrum may measure the plurality of spectra by changing a target signal in the in-vivo or in-vitro environment.

Then, the apparatus 100 for obtaining a target signal spectrum may obtain a difference spectrum matrix by subtracting a reference spectrum from each of the measured spectra in 620.

Subsequently, the apparatus 100 for obtaining a target signal spectrum may determine a reference wavelength based on the difference spectrum matrix in 630. The reference wavelength may be a wavelength at which a change in spectrum absorbance is greatest according to a change in target signal, or a wavelength at which an absorption coefficient of the target material is highest, in the difference spectrum matrix.

Next, the apparatus 100 for obtaining a target signal spectrum may obtain a target signal spectrum by calculating an inner product between a shift vector of the reference wavelength and shift vectors of all the wavelengths in the difference spectrum matrix in 640. As described above, upon obtaining the target signal spectrum, the apparatus 100 for obtaining a target signal spectrum may scale an amplitude of the obtained target signal spectrum based on a pre-defined reference target signal spectrum.

Figure 7:
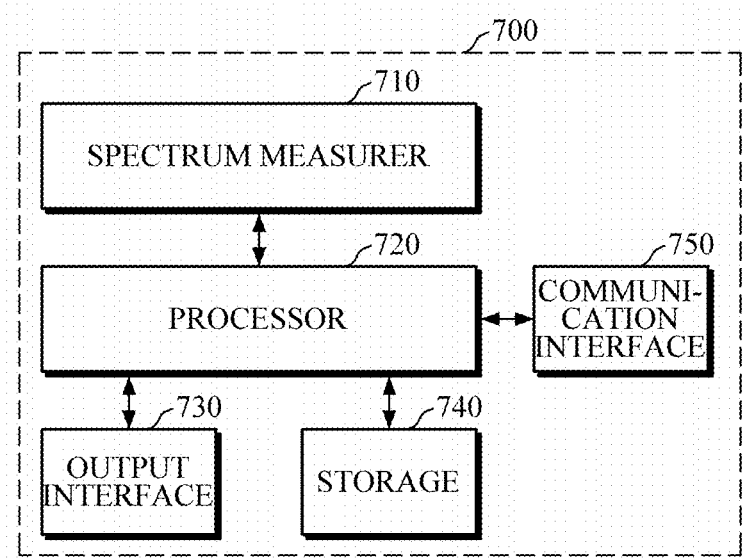
FIG. 7 is a block diagram illustrating an apparatus for estimating a target signal according to an example embodiment.

FIG. 7 is a block diagram illustrating an apparatus for estimating a target signal according to an example embodiment.

The apparatus 700 for estimating a target signal according to an embodiment may estimate a target signal by using a technique for obtaining a target signal described above. Examples of the target signal include blood glucose, cholesterol, triglyceride, protein, uric acid, and the like. For convenience of explanation, the following description will be given using blood glucose as an example.

Referring to FIG. 7, the apparatus 700 for estimating a target signal includes a spectrum measurer 710, a processor 720, an outputter 730, a storage 740, and a communicator (or communication interface) 750.

The spectrum measurer 710 may include a spectrometer for measuring spectra over a wide wavelength range, or an optical sensor for measuring spectra over a relatively narrow wavelength range. The spectrum measure 710 may measure the spectra by emitting light onto the surface of a user's skin and detecting light reflected from the surface of the user's skin or light scattered or reflected from the surface of blood vessels or substances in the blood vessels.

The processor 720 may be electrically connected to the spectrum measurer 710. In response to a request for estimating a blood glucose signal, the processor 720 may control the spectrum measurer 710 to obtain spectra. The processor 720 may control the spectrum measurer 710 to continuously measure a plurality of spectra for a predetermined period of time at predetermined time intervals. Alternatively, once the spectrum measurer 710 measures a spectrum at a current time, the processor 720 may extract one or more spectra, obtained at a previous time, from the storage 740.

For example, by using the plurality of spectra measured by the spectrum measurer 710 for a predetermined period of time, or by using the spectrum at the current time and one or more spectra at the previous time which are extracted from the storage 740, the processor 720 may obtain a blood glucose signal spectrum.

For example, the processor 720 may obtain a difference spectrum matrix by subtracting a reference spectrum from the plurality of spectra, and may obtain a blood glucose signal spectrum by using the obtained difference spectrum. For example, the processor 720 may generate a symmetric matrix by multiplying the difference spectrum matrix by a transposed matrix of the difference spectrum matrix, and may obtain a blood glucose signal spectrum by selecting any one row or column from the symmetric matrix. In another example, the processor 720 may also obtain a blood glucose signal spectrum by multiplying a shift vector of a wavelength, at which a change in the target signal is greatest, by a shift vector of each wavelength in the difference spectrum. Upon obtaining the blood glucose signal spectrum, the processor 720 may scale an amplitude of the obtained blood glucose signal spectrum based on the reference blood glucose signal spectrum stored in the storage 740.

Upon obtaining the blood glucose signal spectrum, the processor 720 may estimate a blood glucose signal by using the blood glucose signal spectrum. For example, the processor 720 may estimate a blood glucose signal from the blood glucose signal spectrum by using a blood glucose estimation model pre-defined by Net Analyte Signal (NAS) analysis based on Beer Lambert's Law, but is not limited thereto.

In another example, once the spectrum measurer 110 measures the spectrum at the current time, the processor 720 may extract a unit spectrum of a blood glucose signal from the storage 740, and may estimate blood glucose based on the extracted unit spectrum and the spectrum measured at the current time by using the blood glucose estimation model pre-defined based on Beer Lambert's Law. In this case, the unit spectrum may be a blood glucose signal spectrum obtained from, e.g., an aqueous solution, by the aforementioned apparatus 100 for obtaining a target signal spectrum. The processor 720 may receive the blood glucose signal spectrum from the apparatus 100 for obtaining a target signal spectrum through the communicator 750 and may store the received blood glucose signal spectrum in the storage 740.

In yet another example, once the apparatus 100 for obtaining a target signal spectrum obtains a spectrum of a noise signal such as temperature, the processor 720 may receive the noise signal spectrum through the communicator 750 and may store the received noise signal spectrum in the storage 740. Further, the processor 720 may update the blood glucose estimation model by reflecting the noise signal spectrum in the blood glucose estimation model. In addition, once the spectrum measurer 110 measures the spectrum at the current time, the processor 720 may estimate blood glucose based on the blood glucose estimation model.

The outputter (or output interface) 730 may provide processing results of the processor 720 for a user. For example, the outputter 730 may display a processing result of the processor 720, e.g., an estimated blood glucose value, on a display. In this case, if the estimated blood glucose value falls outside a normal range, the outputter 730 may provide a user with warning information by changing color, line thickness, etc., or displaying the abnormal value along with a normal range, so that the user may easily recognize the abnormal value. Further, along with the visual display or alone, the outputter 730 may provide a substance analysis result in a non-visual manner by voice, vibrations, tactile sensation, and the like using a voice output module such as a speaker, or a haptic module and the like.

The storage 740 may store reference information to be used for estimating a target signal, and processing results of the spectrum measurer 710 and/or the processor 720. For example, the reference information may include user characteristic information, such as a user's age, gender, health condition, and the like. Further, the reference information may include a blood glucose estimation model, a reference spectrum, and the like.

The storage 740 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

The communicator 750 may communicate with an external device to transmit and receive various data, such as a target signal spectrum and the like, to and from the external device. In this case, the external device may include an information processing device such as a smartphone, a tablet PC, a desktop computer, a laptop computer, and the like. For example, the communicator 750 may transmit a blood glucose estimation result to a user's smartphone and the like, so that the user may manage and monitor blood glucose by using a device having a relatively high performance. However, the communicator 750 is not limited thereto.

The communicator 750 may communicate with the external device by using various wired or wireless communication techniques, such as Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. However, this is merely exemplary and is not intended to be limiting.

Figure 8:
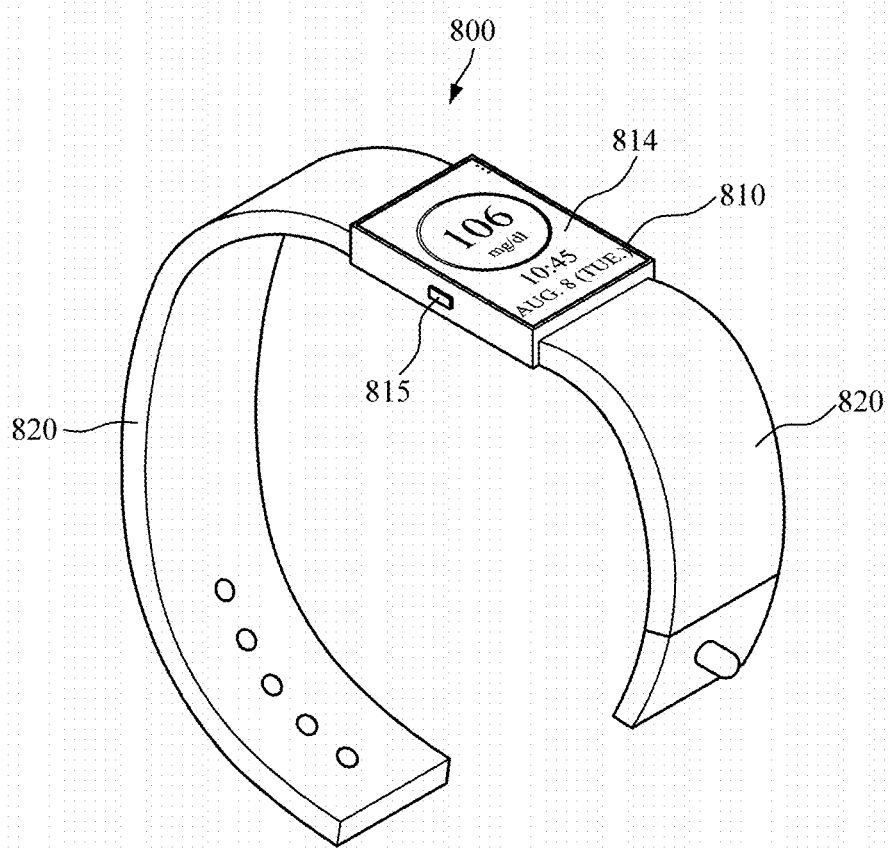
FIG. 8 is a diagram illustrating a wearable device according to an example embodiment.

FIG. 8 is a diagram illustrating a wearable device according to an example embodiment. Various embodiments of the apparatus 700 for estimating a target signal may be mounted in a wearable device such as a smart band or a smart watch as illustrated in FIG. 8, but the apparatus 700 for estimating a target signal is not limited thereto and may be mounted in a smart device, such as a smartphone, a tablet PC, smart earphones, smart glasses, and the like, or in an information processing device such as a desktop computer, a laptop computer, and the like.

Referring to FIG. 8, the wearable device 800 includes a main body 810 and a strap 820.

The main body 810 may be worn on a user's wrist with the strap 820. The main body 810 may include various modules to perform various functions of the wearable device 800. A battery may be embedded in the main body 810 or the strap 820 to supply power to the various modules of the wearable device 800. The strap 820 may be connected to both ends of the main body 810, and may be flexible so as to be wrapped around a user's wrist. The strap 820 may include a first strap and a second strap which are separated from each other. One ends of the first strap and the second strap are connected to the main body 810, and the other ends thereof may be connected to each other via a connecting means. In this case, the connecting means may be formed as magnetic connection, Velcro connection, pin connection, and the like, but is not limited thereto. Further, the strap 820 is not limited thereto, and may be integrally formed as a non-detachable band.

The main body 810 may include a spectrum measurer. As described above, the spectrum measurer includes a light source and a detector, and may measure spectra from a user.

A processor may be mounted in the main body 810. The processor may be electrically connected to various modules of the wearable device 800. The processor may obtain a blood glucose signal spectrum based on the spectra measured by the spectrum measurer, and may obtain a blood glucose signal by using the obtained blood glucose signal spectrum. Further, the processor may estimate a blood glucose signal by using a unit spectrum of the blood glucose signal which is obtained by the apparatus for obtaining a target signal spectrum.

Further, the main body 810 may include a storage which stores a variety of reference information and information processed by the various modules.

In addition, the main body 810 may include a manipulator 815 which is provided on one side surface of the main body 810, and receives a user's control command and transmits the received control command to the processor. The manipulator 815 may have a power button to input a command to turn on/off the wearable device 800.

Further, a display 814 for outputting information to a user may be mounted on a front surface of the main body 810. The display 814 may have a touch screen for receiving touch input. The display 814 may receive a user's touch input and transmit the touch input to the processor, and may display processing results of the processor.

Moreover, the main body 810 may include a communicator for communication with an external device. The communicator may transmit a blood glucose estimation result to the external device, e.g., a user's smartphone, and may obtain a unit spectrum of a blood glucose signal from the apparatus for obtaining a blood glucose signal spectrum.

The disclosure may be implemented as a computer-readable code written on a computer-readable recording medium. The computer-readable recording medium may be any type of recording device in which data is stored in a computer-readable manner.

Examples of the computer-readable recording medium include a ROM, a RAM, a CD-ROM, a magnetic tape, a floppy disc, an optical data storage, and a carrier wave (e.g., data transmission through the Internet). The computer-readable recording medium may be distributed over a plurality of computer systems connected to a network so that a computer-readable code is written thereto and executed therefrom in a decentralized manner. Functional programs, codes, and code segments for implementing the disclosure may be readily deduced by programmers of ordinary skill in the art to which the disclosure pertains.

At least one of the components, elements, modules or units described herein may be embodied as various numbers of hardware, software and/or firmware structures that execute respective functions described above, according to an example embodiment. For example, at least one of these components, elements or units may use a direct circuit structure, such as a memory, a processor, a logic circuit, a look-up table, etc. that may execute the respective functions through controls of one or more microprocessors or other control apparatuses. Also, at least one of these components, elements or units may be specifically embodied by a module, a program, or a part of code, which contains one or more executable instructions for performing specified logic functions, and executed by one or more microprocessors or other control apparatuses. Also, at least one of these components, elements or units may further include or implemented by a processor such as a central processing unit (CPU) that performs the respective functions, a microprocessor, or the like. Two or more of these components, elements or units may be combined into one single component, element or unit which performs all operations or functions of the combined two or more components, elements of units. Also, at least part of functions of at least one of these components, elements or units may be performed by another of these components, element or units. Further, although a bus is not illustrated in the block diagrams, communication between the components, elements or units may be performed through the bus. Functional aspects of the above example embodiments may be implemented in algorithms that execute on one or more processors. Furthermore, the components, elements or units represented by a block or processing operations may employ any number of related art techniques for electronics configuration, signal processing and/or control, data processing and the like.

Several example embodiments have been described above. However, it will be obvious to those skilled in the art that various changes and modifications may be made without changing technical conception and essential features of the disclosure. Thus, it is clear that the above-described embodiments are illustrative in all aspects and are not intended to limit the disclosure.

What is claimed is:

1. An apparatus for non-invasively estimating bio-information based on a target signal spectrum, the apparatus comprising:
    a spectrum measurer configured to measure a plurality of spectra from an object; and
    a processor configured to obtain a difference spectrum matrix by subtracting a reference spectrum from each of the plurality of spectra, to obtain a spectrum of a target signal based on the obtained difference spectrum matrix, and to estimate bio-information of the object based on the spectrum of the target signal by using a bio-information estimation model,
    wherein the processor is further configured to obtain a symmetric matrix by calculating an inner product between the difference spectrum matrix and a transposed matrix of the difference spectrum matrix, select one row or one column from the obtained symmetric and obtain the spectrum of the target signal based on the selected one rover or one column,
    wherein the target signal comprises at least one body substance and at least one noise component, and
    wherein the processor is configured to, based on a spectrum of the at least one noise component being obtained, update the bio-information estimation model by reflecting the spectrum of the at least one noise component in the bio-information estimation model.

2. The apparatus of claim 1, wherein the spectrum measurer comprises:
    a light source configured to emit light onto the object; and
    a detector configured to detect light scattered or reflected from the object.

3. The apparatus of claim 1, wherein the spectrum measurer is further configured to measure the plurality of spectra continuously at predetermined time intervals in an in-vivo environment or an in-vitro environment in which the target signal changes.

4. The apparatus of claim 1, wherein the reference spectrum comprises, among the plurality of spectra, at least one of a spectrum measured at a predetermined time, an average spectrum of the plurality of spectra, a spectrum measured in a fasting state when the plurality of spectra are measured in an in-vivo environment, or a spectrum measured in an aqueous solution when the plurality of spectra are measured in an in-vitro environment.

5. The apparatus of claim 4, wherein the processor is further configured to remove noise from the measured plurality of spectra based on one or more of second-order differentiation, filtering, asymmetric least square (ALS), detrend, multiplicative scatter correction (MSC), extended multiplicative scatter correction (EMSC), standard normal variate (SNV), mean centering (MC), fourier transform (FT), orthogonal signal correction (OSC), and Savitzky-Golay smoothing (SG).

6. The apparatus of claim 1, wherein the processor is further configured to select the one row or the one column from the obtained symmetric matrix based on a degree of change in the target signal.

7. The apparatus of claim 1, wherein the processor is further configured to select a row or a column of a wavelength, at which a degree of change in the target signal is greatest, or select a row or a column of a wavelength, at which a degree of absorption of the target signal is highest, from the obtained symmetric matrix.

8. The apparatus of claim 1, wherein the processor is further configured to scale an amplitude of the obtained spectrum of the target signal to correspond to an amplitude of a reference target signal spectrum.

9. The apparatus of claim 1, wherein the target signal comprises one or more of an antioxidant-related substance, blood glucose, triglyceride, cholesterol, calories, protein, carotenoid, lactate, and uric acid.

10. A method of non-invasively estimating bio-information based on a target signal spectrum, the method comprising:
measuring a plurality of spectra from an object;
obtaining a difference spectrum matrix by subtracting a reference spectrum from each of the plurality of spectra; and
obtaining a spectrum of a target signal based on the obtained difference spectrum matrix and estimating bio-information of the object based on the spectrum of the target signal by using a bio-information estimation model,
wherein the obtaining the spectrum of the target signal comprises:
obtaining a symmetric matrix by calculating an inner product between the difference spectrum matrix and a transposed matrix of the difference spectrum matrix;
selecting one row or one column from the obtained symmetric matrix; and
obtaining the spectrum of the target signal based on the selected one row or one column,
wherein the target signal comprises at least one body substance and at least one noise component, and
wherein the method further comprises, based on a spectrum of the at least one noise component being obtained, updating the bio-information estimation model by reflecting the spectrum of the at least one noise component in the bio-information estimation model.

11. The method of claim 10, wherein the reference spectrum comprises, among the plurality of spectra, at least one of a spectrum measured at a predetermined time, an average spectrum of the plurality of spectra, a spectrum measured in a fasting state when the plurality of spectra are measured in an in-vivo environment, or a spectrum measured in an aqueous solution when the plurality of spectra are measured in an in-vitro environment.

12. The method of claim 10, further comprising removing noise from the measured plurality of spectra based on one or more of second-order differentiation, filtering, asymmetric least square (ALS), detrend, multiplicative scatter correction (MSC), extended multiplicative scatter correction (EMSC), standard normal variate (SNV), mean centering (MC), fourier transform (FT), orthogonal signal correction (OSC), and Savitzky-Golay smoothing (SG).

13. The method of claim 10, wherein the selecting comprises selecting the one row or the one column from the obtained symmetric matrix based on a degree of change in the target signal.

14. The method of claim 10, wherein the obtaining the spectrum of the target signal comprises scaling an amplitude of the obtained spectrum of the target signal to correspond to an amplitude of a reference target signal spectrum.

15. The apparatus of claim 1, further comprising an output interface configured to provide a result of estimating the bio-information.

16. The apparatus of claim 15, wherein the output interface is further configured to, based on the estimated bio-information being outside a normal range, output warning information related to an abnormal value of the estimated bio-information using at least one of a visual manner or a non-visual manner.

17. An apparatus for non-invasively estimating bio-information based on a target signal spectrum, the apparatus comprising:
a spectrum measurer configured to measure a plurality of spectra from an object; and
a processor configured to obtain a difference spectrum matrix by subtracting a reference spectrum from each of the plurality of spectra, to obtain a spectrum of a target signal based on the obtained difference spectrum matrix, and to estimate bio-information of the object based on the spectrum of the target signal by using a bio-information estimation model,
wherein the processor is further configured to calculate an inner product between a shift vector of a predetermined wavelength and shift vectors of other wavelengths in the difference spectrum matrix, and obtain the spectrum of the target signal based on the calculated inner product,
wherein the target signal comprises at least one body substance and at least one noise component, and
wherein the processor is configured to, based on a spectrum of the at least one noise component being obtained, update the bio-information estimation model by reflecting the spectrum of the at least one noise component in the bio-information estimation model.

* * * * *